United States Patent [19]

Powell et al.

[11] 4,453,404

[45] Jun. 12, 1984

[54] METHOD AND APPARATUS FOR DETERMINING STATISTICAL CHARACTERISTICS OF SHEET MATERIAL

[75] Inventors: Calvin J. Powell, Miamisburg; Robert R. Rounsley, Chillicothe, both of Ohio

[73] Assignee: The Mead Corporation, Dayton, Ohio

[21] Appl. No.: 443,351

[22] Filed: Nov. 22, 1982

[51] Int. Cl.$^3$ .......................... G06G 7/66; G06G 7/12
[52] U.S. Cl. ........................................ 73/159; 364/471
[58] Field of Search .......................... 73/159; 325/473; 364/471, 472, 572

[56] References Cited

U.S. PATENT DOCUMENTS

| | | | |
|---|---|---|---|
| 3,496,344 | 2/1970 | Chope | 364/572 X |
| 3,557,351 | 1/1971 | Doering | 364/572 |
| 3,636,327 | 1/1972 | Troutman | 235/151.33 |
| 3,703,097 | 11/1972 | Kilpatrick | 73/159 |
| 3,826,132 | 7/1974 | Fetner | 73/159 X |
| 3,847,730 | 11/1974 | Doering | 162/198 |
| 3,850,031 | 11/1974 | Schuenpeier | 73/159 X |
| 3,914,585 | 10/1975 | Wilhelm | 73/159 X |
| 3,974,248 | 8/1976 | Atkinson | 73/159 X |
| 4,045,659 | 8/1977 | Akagawa | 364/470 |
| 4,309,902 | 1/1982 | Sand | 73/159 |
| 4,404,634 | 9/1983 | Bautz | 73/159 X |

OTHER PUBLICATIONS

"The Application of Extreme-Value Theory to Error-Free Communication" Edward C. Posner, *Technometrics*, vol. 7, No. 4, pp. 517-529—Nov. 1965.
"Extremal Statistics in Computer Simulation of Digital Communication Systems" Schwartz & Richman, *Extremal Statistics in Computer Simulation*, 1968, pp. 483-489.

*Primary Examiner*—S. Clement Swisher
*Assistant Examiner*—Vincent P. Koualick
*Attorney, Agent, or Firm*—Biebel, French & Nauman

[57] ABSTRACT

A method for determining statistical characteristics of a measurable property includes the initial step of monitoring the property and generating an electrical signal, the magnitude of which is a representative measure of the property. The electrical signal is passed through a high pass filter to eliminate low frequency noise which would otherwise tend to affect artificially extreme values of the signal. The maxima of the filtered signal is then determined within defined time intervals and extreme value statistical analysis is applied to the maxima of the filtered electrical signal to determine statistical characteristics of the measurable property. This method and apparatus for performing the method may be favorably applied to monitoring weight basis of sheet material, such as paper, as the material is being produced.

20 Claims, 5 Drawing Figures

METHOD AND APPARATUS FOR DETERMINING STATISTICAL CHARACTERISTICS OF SHEET MATERIAL

BACKGROUND OF THE INVENTION

This invention relates generally to systems for monitoring physical properties and, more particularly, to a method and apparatus for determining statistical characteristics of the physical properties of material, such as the sheet material, as it is being produced.

While the present invention has a large variety of applications, it is particularly applicable in the production of paper and, hence, will be described with reference to paper manufacture. Upon review of the following description, however, it will be appreciated that the present invention may be used in many other situations in which a varying physical property is monitored. In many such situations, it is not feasible to sample, store, and analyse the physical property values at a sample rate sufficient to reflect the fluctuations in the property. The present invention provides a practical way of developing meaningful statistical indicia relating to the property without storing all of the sampled values.

It is well known in the prior art to monitor characteristics of a paper web as it is being produced to determine and control the averages of those characteristics. For example, moisture, basis weight and caliper may be monitored and the resulting signals utilized in feedback control systems to maintain the averages of the properties within required specification limits.

While such process control systems are known in the prior art and perform well in maintaining the averages of a variety of properties of the paper web within desired specifications, peak variations in the properties still occur during the paper manufacturing process. Since paper is graded according to the monitored properties of the paper web and the deviations of those properties from defined specifications, it is important to be able to quantify the properties and their deviations to classify the paper for further processing and sale.

As paper is manufactured, it is formed into rolls which are oftentimes immediately transferred from the paper making machine to the next processing station where the rolls are cut into desired sheet sizes and packaged for shipment to fill orders requiring various specifications. Accordingly, it is important to be able to monitor and analyze the properties of the paper web rapidly to prevent delays in the manufacturing process.

In the prior art, the properties of a roll of paper are normally averaged over segments of paper tens of feet long due to the paper machine operating speeds and the time constants of the monitoring gauges. Since the paper is to be cut into small sheets, for example $8\frac{1}{2}$ inches by 11 inches, the averaging of the characteristics of the paper over long segments overlooks individual discrepancies or fluctuations in the properties which may appear in one or many of the sheets which are cut from the paper roll.

It is thus apparent that a need exists for an improved method and apparatus for determining statistical characteristics of measurable properties of sheet material as the sheet material is being produced so that timely decisions can be made as to the classification and appropriate further processing of the sheet material.

SUMMARY OF THE INVENTION

In accordance with the present invention, physical characteristics of a web of material are measured, for example, by providing gauge means adjacent to a moving web of material as the material is manufactured. The response time of the gauge means is made quite fast, in the order of milliseconds, so that rapid variations in the measured characteristic of the sheet material can be accurately detected by the gauge means. This is particularly important in the case of paper manufacture since, by the selection of a rapid response time, characteristics of individual sections of the paper web which correspond approximately in size to the final paper sheets to be cut from that web can be measured by the gauge means.

In the prior art, such high speed monitoring has been considered undesirable since an average of a measured characteristic is typically utilized to control the manufacture of the web of sheet material. Also, such rapid measurements provide even greater amounts of data which require correspondingly greater periods of time to process to determine the statistical characteristics for the sheet material. Finally, the electrical signal from the gauge means for measurements taken at such close intervals tends to have considerable low frequency noise which affects the maxima and minima of the signal and, hence, the measured extrema of the property. Such low frequency noise can be generated, for example, by movements of the gauge means across the web and even by the gauge means itself for certain constructions of the gauge means.

Apparatus in accordance with the present invention provides high pass filter means connected to the gauge means for receiving the electrical signal representative of variations in the measured property thereby to eliminate low frequency noise due to cross-machine motion and/or inherent to the gauge means utilized.

The problem of massive amounts of data as previously described is indeed amplified by the high speed measurements made by the gauge means. However, this problem is overcome by utilizing only the extreme values of the electrical signals generated by the gauge means. Analyzer means are provided for generating statistical characteristics of the measured property of the sheet material in response to the extreme values of the filtered electrical signal by means of extreme value statistical analysis. That is, the maxima and/or minima of the electrical signal which occurs over given time intervals of monitoring are analyzed by means of extreme value statistical analysis.

In the preferred embodiment of the present invention, the determination of the extreme electrical signal values is made by peak detection means connected to the high pass filter means for determining the maximum value of the filtered electrical signal, sample and hold means for reading the peak detection means, and timing means for periodically clearing the peak detection means and the sample and hold means. Minima of the electrical signals can be similarly determined by inverting the signal, detecting the peaks of the signal, and holding them in sample and hold means until they are passed to analyzer means typically comprising a computer.

Also disclosed is a method for determining statistical characteristics of a measurable property of sheet material as the sheet material is being produced comprising the steps of: monitoring the sheet material at an appropriate stage of production to generate an electrical signal the magnitude of which is representative of a property of the sheet material; passing the electrical signal through a high pass filter to eliminate low frequency noise which tends to artificially affect extreme values of the electrical signal; determining the maxima of the filtered electrical signal which occur within defined time intervals; and applying extreme value statistical analysis to the maxima of the filtered electrical signal to determine statistical characteristics of the measured property of the sheet material.

Additional steps may include determining the minima of the filtered electrical signal which occur within defined time intervals and applying extreme value statistical analysis to the minima of the filtered electrical signal to determine statistical characteristics of the measured property of the sheet material. The monitoring step preferably comprises scanning the sheet material by sweeping a property measuring gauge laterally across a moving web of the material. When the sheet material is paper, the defined time intervals correspond to motion of the gauge across portions of the web, which portions are separated to form individual rolls of paper.

The method can further comprise passing the electrical signal through a low pass filter to eliminate high frequency noise prior to the determination of the maxima and/or minima of the filtered electrical signal such that high frequency noise is eliminated and prevented from producing artificial maxima and/or minima of the electrical signal. The determination of the maxima and minima is preferably performed by passing the filtered signal to a peak detector to determine the maxima, and inverting the filtered signal and passing the inverted filtered signal to a peak detector to determine the minima of the filtered signal. The maxima and/or minima of the signal is passed to a computer which applies extreme value statistical analysis to arrive at statistical characteristics of the measurable property of the sheet material.

It is, therefore, an object of the present invention to provide an improved method and apparatus for determining statistical characteristics of a measurable property.

It is another object of the present invention to provide an improved method and apparatus for determining the statistical characteristics of sheet material by measuring the properties of the sheet material with a gauge having a rapid response time, such that properties of individual sections of the sheet material, which correspond in size to final sheets to be cut therefrom, are measured by the gauge.

It is yet another object of the present invention to provide an improved method and apparatus for determining statistical characteristics of sheet material by monitoring properties of the material and determining the maxima and/or minima of the properties within defined time periods of measurement and applying extreme value statistical analysis to determine the statistical characteristics of the measurable properties of the sheet material.

Other objects and advantages of the invention will be apparent from the following description, the accompanying drawings and the appended claims.

DETAILED DESCRIPTION OF THE INVENTION

Figures 1, 4:
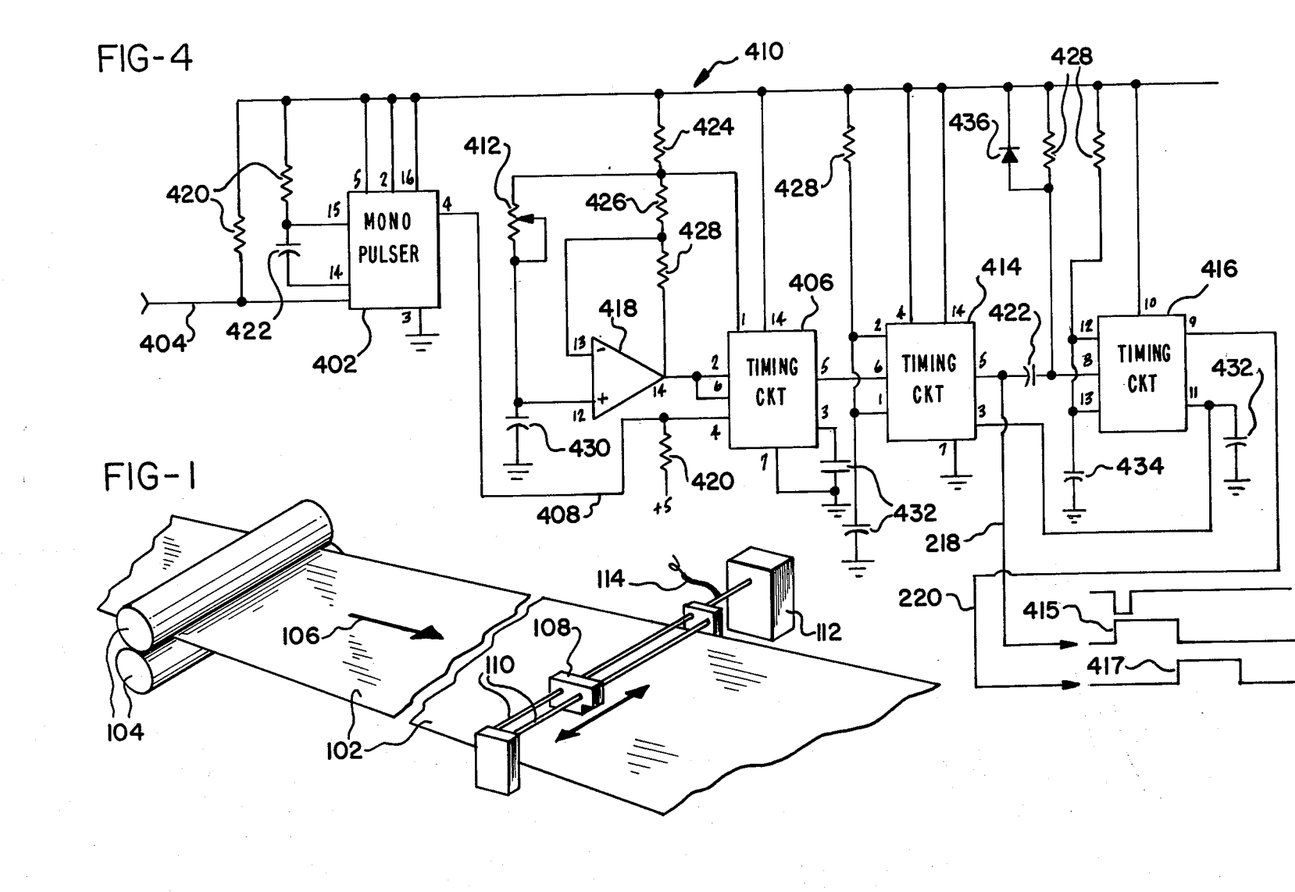
FIG. 1 is a perspective view of a typical application of the present invention to the manufacture of a paper web.
FIG. 4 is a schematic diagram of a control circuit utilized to synchronize the operation of the circuitry shown in FIG. 3B for defining a variety of timing intervals during which maxima and minima are detected.

In FIG. 1, a web of material 102, such as paper, is passed from a manufacturing machine, represented by calender rollers 104, in the direction of the arrow 106. Gauge means 108 is supported for movement along guidebars 110 so that the gauge means 108 can be swept back and forth across the web of material 102. The gauge means 108 monitors at least one property of the web of material 102, for example, basis weight, as the gauge means 108 is swept back and forth across the moving web.

Such monitoring of the properties of a web of material is well known in the art with an electrical signal from the gauge means 108 being passed to a control system 112 via conductors 114. The system 112, among other functions, controls the web manufacturing machine to maintain the average of measured properties within prescribed specification limits. Such gauge means in the prior art typically have relatively large response times or time constants, on the order of 1.1 seconds for a scan mode of the gauge 108, and 100 milliseconds for a fixed mode with the speed of the web being approximately 2000 feet per minute.

Figure 2:
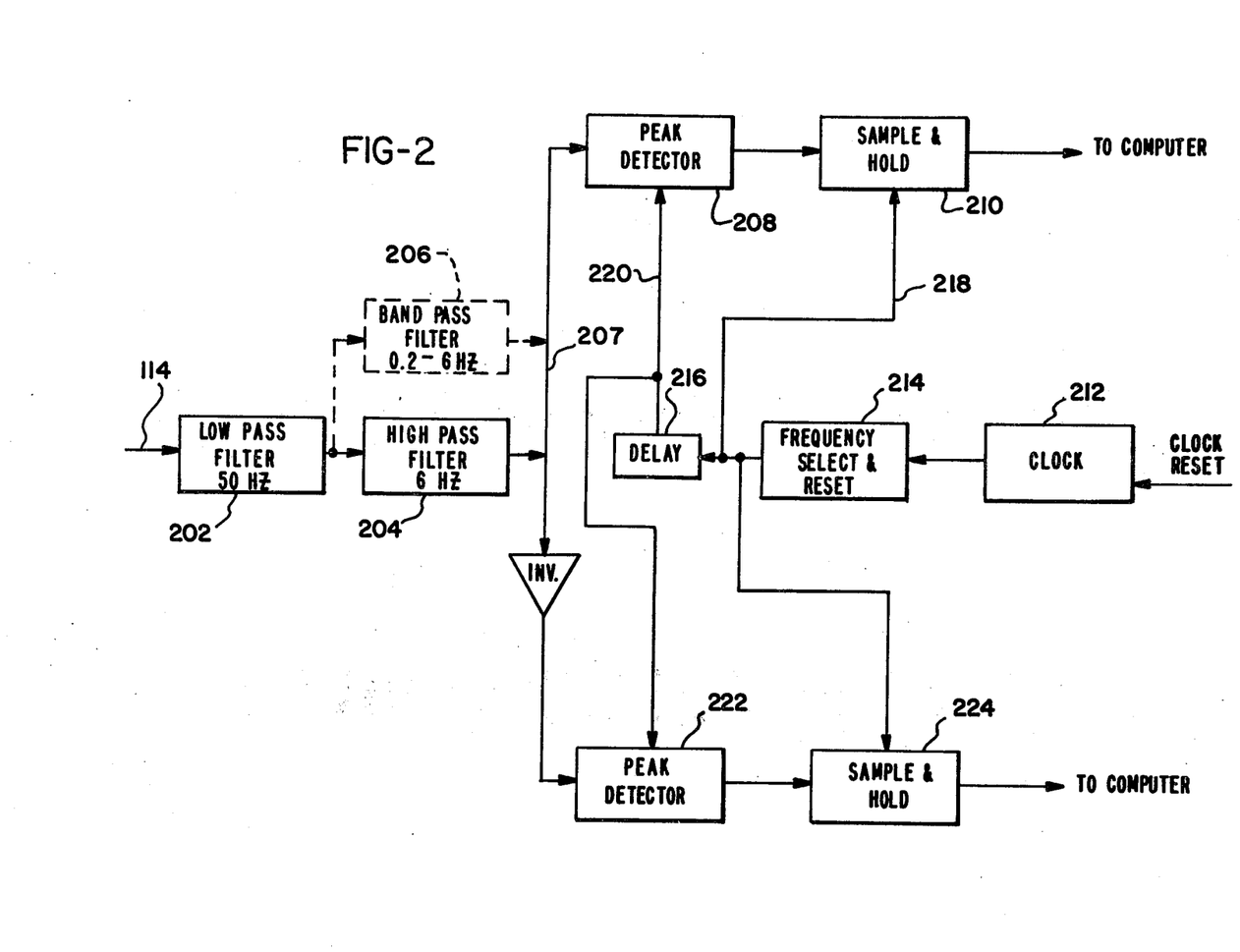
FIG. 2 is a block diagram of the circuitry utilized to determine the maxima and minima of an electrical signal generated by the gauge means of FIG. 1.

To apply extreme value statistics to the signals generated by the gauge means 108, selected time intervals are defined and the maximum and/or minimum of the electrical signal is determined during each of the time intervals. While this function could be performed by a computer, the determination of the maxima and/or minima of the electrical signal within these time intervals would be quite time consuming and in essence would defeat the purpose of the present invention which is to provide rapid analysis during the production of sheet material. Accordingly, the electrical signal from the gauge means 108 is passed to a signal conditioning and detecting circuit as shown in FIG. 2 which may be located for example within the system 112.

The signal is passed through a low pass filter 202 to filter out high frequency noise which might otherwise be interpreted as an extreme value of the electrical signal from the gauge means 108. The signal from the low pass filter 202 is passed to a high pass filter 204 to filter out low frequency noise due to scanning across the web and the design of the gauge means 108. Such low frequency noise would otherwise affect the magnitude of the extreme values of the electrical signal from the gauge means 108. If the variations in the cross machine direction are to be monitored, the high pass filter 204 can be replaced by a band pass filter 206 or a duplicated system may be provided which includes the band pass filter 206 and the peak detection circuitry which will now be described.

The output of the high pass filter 204 is connected via conductor 207 to a peak detector 208 which determines the highest voltage level of the signal seen at its input terminal between the time that it is set and reset. The output of the peak detector is connected to the input of a sample and hold circuit 210. The sample and hold circuit 210 is activated during a sampling period to sample the signal on its input and maintain the sampled signal value during a holding period or until the sample and hold circuit is once again placed in a sampling mode. Thus, the peak detector 208 determines the maximum voltage level or peak of the output signal from the high pass filter 204 and the peak value is passed from the peak detector 208 to the sample and hold circuit 210 during a sampling period.

A clock circuit 212 drives a frequency select and reset circuit 214 to periodically activate the sample and hold circuit 210 to the sampling mode and to thereafter clear the peak detector 208 for the next time interval. A delay 216 is interposed to pass the sampling signal on the conductor 218 to the peak detector 208 on the conductor 220 a defined period of time after the output signal of the peak detector is sampled. The timing is such that the sample and hold circuit is activated to "sample and hold" the peak value determined by the peak detector 208 prior to clearing the peak detector. With the peak value of the signal from the high pass filter 204 for the preceding time interval stored in the sample and hold circuit 210, an associated computer which performs the extreme value statistical analysis can read the peak value from the sample and hold circuit 210 at its convenience prior to the next sampling time.

The minimum values of the output signal from the high pass filter 204 are determined by passing the signal through an inverter and again determining the peak value of the signal via a peak detector 222. In this case, the peak value corresponds to the inverted minimum of the signal. The signal from the peak detector 222 is passed to a sample and hold circuit 224. The sample and hold circuit 224 is placed in the sampling mode and the peak detector 222 is cleared as previously described through the output signals from the frequency select and reset circuit 214 via the delay 216. Here again, the computer performing the extreme value statistical analysis reads the sample and hold circuit 224 to determine the extreme minimum values or minima of the output signal from the high pass filter 204.

The filtered signal emerges from the high pass filter 204 as an alternating current signal centered about a positive voltage level which corresponds to a desired average value for the property being measured, such as the basis weight of a paper web. Thus, the maxima and the minima together with the average value are utilized by the computer to determine the magnitude of the maxima and minima deviations from the average value. The computer applies extreme value statistical analysis to these values to arrive at statistical characteristics of the measured property, for example, the percentage of paper sheets of a final size which will be cut from the web whose basis weight will exceed a selected value as will be described hereinafter.

Figure 3A:
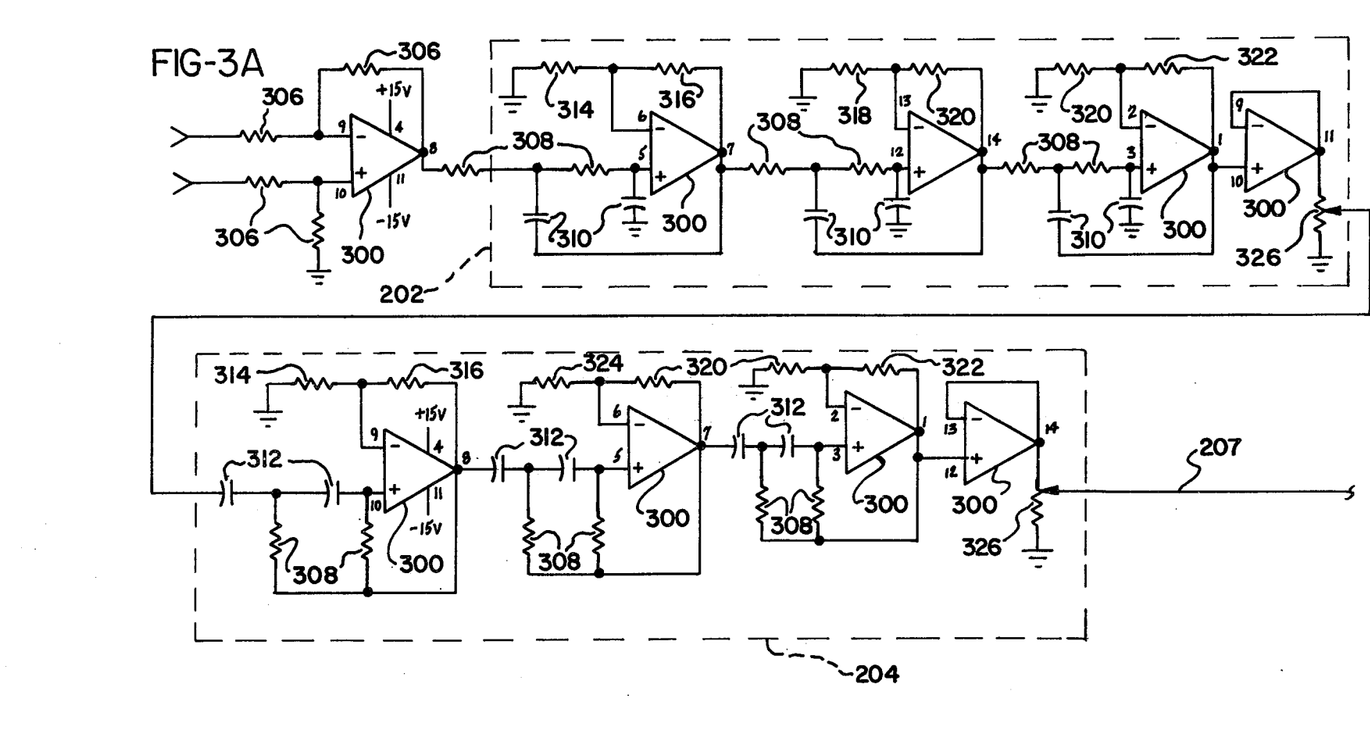
FIGS. 3A and 3B in combination are a schematic diagram of an illustrative embodiment of the signal processing portion of FIG. 2 for filtering and detecting the maxima and minima of the gauge means electrical signal.
Figure 3B:
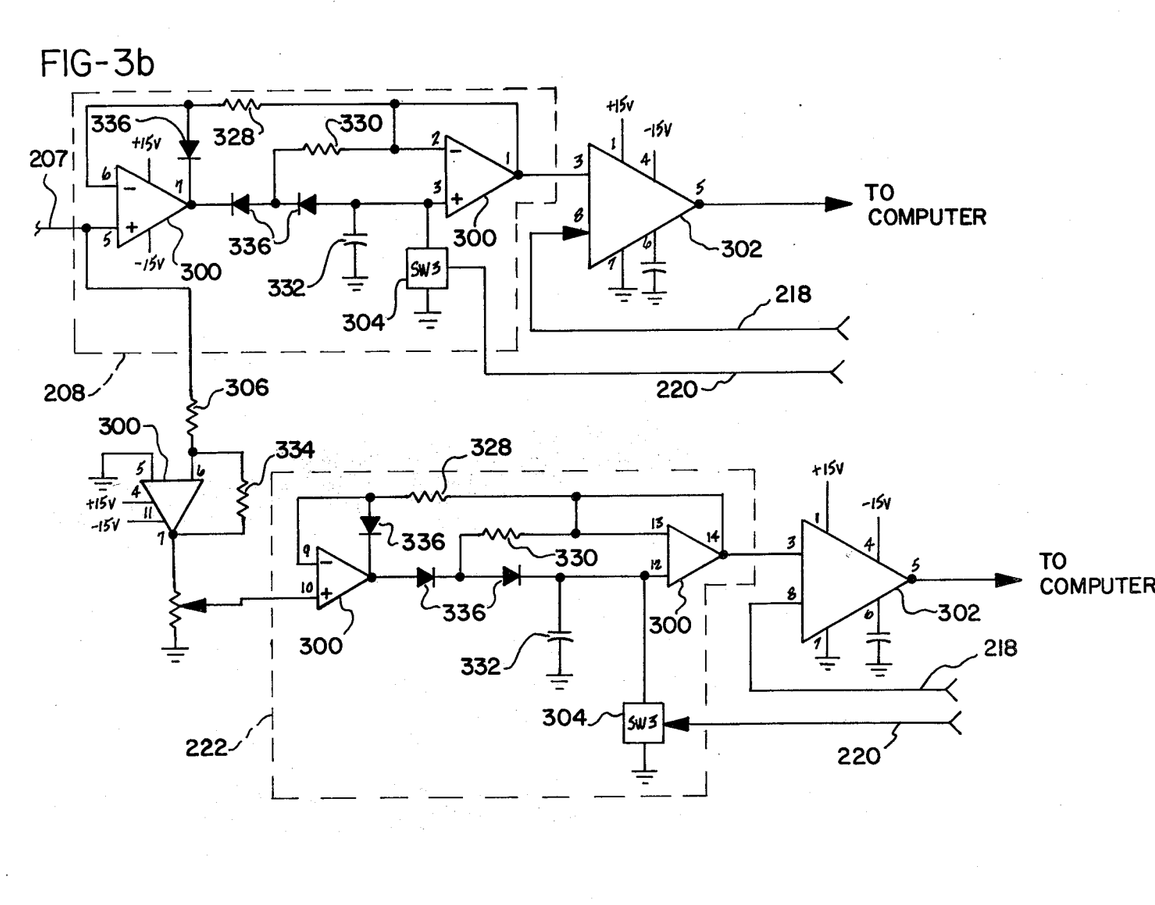

One successful embodiment of the signal conditioning and signal detection functions which permits such rapid processing of the voluminous data generated by the gauge means 108 is illustrated in FIGS. 3A and 3B and has been constructed using the following components:

TABLE I

| | |
|---|---|
| 300 | Operational amplifiers, LM 148, available from National Semiconductor |
| 302 | Sample and hold circuits, LF 198, available from National Semiconductor |
| 304 | Electronic switch, 4066, available from National Semiconductor |
| 306 | Resistors, 1.2 M ohm |
| 308 | Resistors, 100K ohm |
| 310 | Capacitors, 0.033 micro F |
| 312 | Capacitors, 0.33 micro F |
| 314 | Resistors, 3 M ohm |
| 316 | Resistor, 200K ohm |
| 318 | Resistor, 560K ohm |
| 320 | Resistors, 330K ohm |
| 322 | Resistors, 510K ohm |
| 324 | Resistor, 500K ohm |
| 326 | Potentiometers, 10K ohm |
| 328 | Resistors, 20K ohm |
| 330 | Resistors, 220K ohm |
| 332 | Capacitors, 1.0 micro F |
| 334 | Resistor, 1.5 M ohm |
| 336 | Diodes, IN914 |

FIG. 4 is a schematic diagram of a timing circuit for controlling the peak detectors and sample and hold circuits shown in FIGS. 2 and 3B. A monopulser 402 receives an input signal on conductor 404 to generate a synchronizing signal which is passed to a master clock 406 via conductor 408. For example, the signal on the conductor 404 can be generated by the scan control for the gauge means 108 in the system illustrated in FIG. 1 so that a synchronizing signal is generated each time the gauge starts a traverse of the web. In response to the synchronizing signal, a timing circuit 406 serves as a master clock to generate a repetitive sequence of pulses with the repetition rate being determined by the control circuitry 410. By adjustment of a potentiometer 412 of the control circuitry 410, the repetition rate for pulses generated by the timing circuit 406 can be adjusted from microseconds to hours with the repetition rate for a specific application which will be described hereinafter being set at 20 seconds.

The output signal from the timing circuit 406 is passed to a timing circuit 414 which generates a sample pulse 415 on the conductor 218 for the sample and hold circuits 210 and 224 (302) with the end of the sampling pulse triggering a timing circuit 416 to generate a reset pulse 417 on the conductor 220 for resetting the peak detectors 208 and 222. By means of this timing circuitry, the sample and hold circuits 210 and 224 (302) are placed into the sampling mode such that the signals stored in the corresponding peak detectors 208 and 222 are sampled and locked into the sample and hold circuits prior to the generation of a reset pulse for the peak detectors.

Utilization of sample and hold circuits permits the analyzing computer to conveniently select the time at which it reads the extreme values from the circuitry shown in FIG. 2, since the extreme values will be retained in the sample and hold circuits while new values of the electrical signal from the gauge means 108 are monitored by the peak detectors 208 and 222.

One successful embodiment of the timing circuit of FIG. 4 has been constructed using the following components:

TABLE II

| | |
|---|---|
| 402 | Monstable multivibrator, 74123, available from Texas Instruments |
| 406, 414, 416 | Timing circuits, NE/SE556, available from Signetics |
| 412 | Potentiometer, 1.0 M ohm |

TABLE II-continued

| 418 | Operational amplifier, LM 148, available from National Semiconductor |
| 420 | Resistors, 1.0K ohm |
| 422 | Capacitors, 0.033 micro F |
| 424 | Resistor, 47 ohm |
| 426 | Resistor, 1.0 M ohm |
| 428 | Resistor, 10K ohm |
| 430 | Capacitor, 1.0 micro F |
| 432 | Capacitors, 0.01 micro F |
| 434 | Capacitor, 0.1 micro F |
| 436 | Diode, IN914 |

The application of extreme value statistics to determine statistical characteristics of measured properties of sheet material in accordance with the present invention will now be described.

The basic tenet of extreme value statistics is that rather than performing statistical analysis of all samples taken of a given phenomenon, only the extreme values of defined groupings of the samples are analyzed. Thus, given M samples, for example, of the basis weight of a web of paper as it is being manufactured, a group size of n samples per group is determined such that the total number of samples M divides into N groups of n samples each. Next, the extreme values of the samples in each of the N groups must be determined and finally, statistics based on the extreme values of the samples of each group are determined.

In the paper manufacturing illustration shown in FIG. 1, the web 102 is sufficiently wide such that it is divided into several rolls of finished paper by slitting the web parallel to its direction of movement. In one existing system, a web of paper 200 inches wide is divided into three rolls of paper for further processing. In that system, the gauge means 108 is swept across the web laterally so that the web is traversed from one side to the other in one minute. For this existing system, it is convenient to define the groups of samples as comprising the samples taken during 20 seconds of gauge travel time. The groups of samples then individually correspond to one of the rolls of paper to be formed from the web. By properly assembling the groups of samples, it can be seen that the groups can be analyzed to determine the statistical characteristics of all three rolls which are separated from the web 102. The amounts of data utilized for the statistical analysis are drastically reduced since only the extreme value samples from an enormous collection of samples taken over a 20 second period at approximately every few milliseconds are required for the analysis.

Statistics for the sample values of the measured property of the sheet material are computed from the following formulas:

$$\overline{X} = \frac{\sum_{i=1}^{N} X_i}{N}$$

$$\overline{X^2} = \sum_{i=1}^{N} X_i^2$$

$$S^2 = \frac{\overline{X^2} - N(\overline{X})^2}{N-1}$$

where $X_i$ is the largest sample in the ith group of n samples; $\overline{X}$ is the mean of the extreme value samples or the average of all the extreme values of the N groups; and S is the standard deviation of the extreme values.

While these equations provide the mean and the standard deviation of the extreme value samples, extreme value statistics are based on the sample mode and median. The mode and median of the extreme value distribution can be approximated from the sample mean and standard deviation by the Gumbel asymptotic estimates:

$$u_n \approx E(X_m) - \delta/\alpha_n$$

$$1/\alpha_n \approx (\sqrt{6}/\pi)\sigma_m$$

where $u_n$ is a measure of the mode with $\delta$ being Euler's constant, $\delta = 0.5772$; $1/\alpha_N$ is a measure of the dispersion; $E(X_m)$ is the expected value of the extreme value samples; and $\sigma_m$ is the variance of the extreme value samples. $E(X_m)$ is approximated by $\overline{X}$ and $\sigma_m$ is approximated by the standard deviation of the extreme value samples, S. Mathematical techniques such as Newton iteration can be utilized to increase the accuracy of the estimates.

The cumulative probability function for the maximum extreme value is:

$$f(X) = \exp[-\exp[-\alpha(X-u)]]$$

where u is the estimate of the mode and $\alpha$ is the estimate of the dispersion. This equation can be used to calculate the probability of X exceeding the mode. However, we are interested in the probability of X exceeding a given threshold $X_0$ which is given by the equation:

$$f(X_0) = \exp[-\exp[-\alpha(X_0-u)]] = \beta$$

where $X_0$ is the known threshold value which corresponds to a specification for a property of the sheet material, such as basis weight.

The cumulative probability function f(X) can be written in terms of $X_0$ and $\alpha$ as:

$$f(X) = \exp[-\exp[-(\alpha(X-X_0)+v)]]$$

where
$$v = \alpha(X_0 - u)$$

$$-\alpha(X-u) = -\alpha(X-X_0) - \alpha(X_0-u)$$

$$= -[\alpha(X-X_0) + N]$$

and $X_0$ is the given threshold, and $\alpha$ and u are estimated from the measured data as previously described.

The confidence limits of the above approximations can be improved by use of the maximum likelihood estimator. The likelihood function is defined as $$L(X_1, X_2 \ldots X_m; \alpha) = \prod_{K=1}^{n} f(X_K, \alpha)$$

The method of maximum likelihood consists of taking the value of $\alpha$ at which the function L assumes its maximum as an estimate of the parameter $\alpha$. Since L and ln L assume extrema at the same value $\alpha$, the critical values of $\alpha$ are determined from the likelihood equation:

$$\frac{\partial \ln L}{\partial \alpha} = 0$$

Any solution of the likelihood equation is called a maximum likelihood estimate. In our case, $$L(X_1, \ldots X_n; v, \alpha) = \alpha^N \exp(-(\alpha\Sigma(X_i - X_0) + Nv)) \cdot \exp(-\Sigma \exp(-(\alpha(X_i - X_0) + v)))$$

$$\ln L = N \ln \alpha - N\alpha(\overline{X} - X_0) - Nv - \Sigma \exp(-(\alpha(X_i - X_0) + v)) \text{ and the maximum condition } \partial L/\partial X_i = 0$$

$$\frac{\partial \ln L}{\partial \alpha} =$$

$$\frac{N}{\alpha} - N(\overline{X} - X_0) + \Sigma(X_i - X_0)\exp(-(\alpha(X_i - X_0) + v)) = 0$$

$$\frac{\partial \ln L}{\partial v} = N + \Sigma\exp(-(\alpha(X_i - X_0) + v)) = 0$$

gives the implicit values of N and $\alpha$ as:

$$N = \Sigma \exp(-(\alpha(X_i - X_0) + v))$$

$$N/\alpha = N(\overline{X} - X_0) - \Sigma(X_i - X_0)\exp(-(\alpha(X_i - X_0) + v)).$$

However, multiplying N and substituting the expression for N in the expression for $1/\alpha$ gives the likelihood equation:

$$\frac{1}{\alpha} = (\overline{X} - X_0) - \frac{\Sigma(X_i - X_0)\exp(-(\alpha(X_i - X_0) + v))}{\Sigma\exp(-(\alpha(X_i - X_0) + v))}$$

This likelihood equation does not have a closed form solution but can be solved by Newton's iteration techniques using the initial approximations as the zeroth order approximation and the relationship $$X_{i+1} = X_i - \frac{f(X_i)}{f'(X_i)} \quad i = 0, 1, 2 \ldots$$

where $X_{i+1}$ is the new value of $1/\alpha$ to be used in the likelihood equation, $X_i$ is the old value of $1/\alpha$, $f(X_i)$ is the value of the likelihood equation using $X_i$ or $1/\alpha_i$ as its argument.

When the difference between $1/\alpha_{i+1}$ and $1/\alpha_i$ reaches a predefined accuracy level, the iteration is stopped. The value of the mode is calculated from the Gumbel asymptotic estimate as previously given $$u_n \approx \overline{X} - \delta/\alpha_n$$

Knowing the value of $\alpha_n$, $u_n$ and $X_0$, the probability of exceeding the threshold $X_0$ can be calculated as $$1 - \exp(\exp-\alpha_n(X_0 - u_n))$$

where $X_0$ is the threshold, $\alpha_n$ and $u_n$ are the maximum likelihood estimates.

When the present invention is applied to the manufacture of paper and the number of groups of samples N is greater than or equal to approximately five groups, the original estimate is satisfactorily close and, hence, the additional calculations required to improve the confidence levels are not necessary.

Additional understanding and background relative to extreme valve statistical analysis can be had by reference to "Extremal Statistics In Computer Simulation of Digital Communication Systems", Spring Joint Computer Conference, 1968, pp. 483–489 and "The Application of Extreme-Value Theory to Error-Free Communication", Technometrics, Vol. 7, No. 4, November 1965 and the references referred to therein.

While the method herein described and the form of apparatus for carrying this method into effect constitute preferred embodiments of the invention, it is to be understood that the invention is not limited to this precise method and form of apparatus and that changes may be made in either without departing from the scope of the invention which is defined in the appended claims.

It should be understood that the present invention has applicability to a large number of different measurement and analysis problems. As an example, the present invention may be utilized, in conjunction with a vehicle mounted gauge, to provide statistical indicia as to the roughness of a highway. Statistical analysis of any measurable property is enhanced by the use of the present invention.

What is claimed is:

1. A method for determining statistical characteristics of a measurable property, said method comprising the steps of:
    monitoring said property and generating an electrical signal, the magnitude of which is a representative measure of said property;
    passing said electrical signal through a high pass filter to eliminate low frequency noise which would otherwise tend to affect artificially extreme values of said electrical signal;
    determining the maxima of the filtered electrical signal which occurs within defined time intervals; and
    applying extreme value statistical analysis to said maxima of said filtered electrical signal to determine statistical characteristics of said property.

2. The method of claim 1 further comprising the steps of:
    determining the minima of the filtered electrical signal which occurs within said defined time intervals; and
    applying extreme value statistical analysis to said minima of said filtered electrical signal to determine statistical chracteristics of said property.

3. The method of claim 2 further comprising the step of passing said electrical signal through a low pass filter to eliminate high frequency noise prior to the determination of the maxima and minima of said filtered electrical signal, said high frequency noise otherwise potentially being detected as artificial maxima or minima of said electrical signal.

4. The method of claim 3 wherein the step of determining the maxima of the filtered electrical signal comprises the step of passing the filtered signal to a peak detector to determine the maxima of the filtered signal.

5. The method of claim 4 wherein the step of determining the minima of the filtered electrical signal comprises the step of:
    inverting the filtered signal; and
    passing the inverted filtered signal to a peak detector to determine the minima of the filtered signal.

6. The method of claim 5 wherein the step of applying extreme value statistical analysis comprises the steps of:
    passing the maxima of the filtered signal to a computer via a sample and hold circuit;
    passing the minima of the filtered signal to said computer via a sample and hold circuit; and
    applying said computer to determine the statistical characteristics of said sheet material by means of extreme value statistical analysis.

7. Apparatus for determining statistical characteristics of a measurable property, comprising:
- gauge means for monitoring the property of said sheet material and for generating an electrical signal representative of variations in said property;
- high pass filter means, connected to said gauge means, for receiving said electrical signal and eliminating low frequency noise therefrom;
- first peak detection means, connected to said high pass filter means, for determining the maximum value of the filtered electrical signal;
- first sample and hold means for reading said peak detection means;
- timing means for periodically clearing said first peak detection means and said first sample and hold means; and
- analyzer means for generating statistical characteristics of the property by means of extreme value statistical analysis in response to maximum values of said filtered electrical signal read from said first sample and hold means.

8. The apparatus of claim 7 further comprising:
- inverter means, connected to said filter means, for inverting said filtered electrical signal;
- second peak detector means, connected to said inverter means, for determining the minimum values of said filtered electrical signal; and
- second sample and hold means for reading said second peak detector, said timing means being connected to clear periodically said second peak detector means and said second sample and hold means, and said analyzer means further generating selected statistical characteristics of the property in response to minimum values of said filtered electrical signals read from said second sample and hold means by means of extreme value statistical analysis.

9. A method for determining statistical characteristics of a measurable property of sheet material, said method comprising the steps of:
- monitoring said sheet material to generate an electrical signal the magnitude of which is a representative measure of said property of said sheet material;
- passing said electrical signal through a high pass filter to eliminate low frequency noise which would otherwise tend to affect artificially extreme values of said electrical signal;
- determining the maxima of the filtered electrical signal which occurs within defined time intervals; and
- applying extreme value statistical analysis to said maxima of said filtered electrical signal to determine statistical characteristics of said measurable property of said sheet material.

10. The method of claim 9 further comprising the steps of:
- determining the minima of the filtered electrical signal which occurs within said defined time intervals; and
- applying extreme value statistical analysis to said minima of said filtered electrical signal to determine statistical characteristics of the measured property of said sheet material.

11. The method of claim 10 wherein said monitoring step comprises scanning said sheet material by sweeping a measuring gauge laterally across a moving web of said sheet material.

12. The method of claim 11 wherein said sheet material is paper and said defined time intervals correspond to the motion of said gauge across portions of said web, which portions are to be separated subsequently to form individual rolls of paper.

13. The method of claim 10 further comprising the step of passing said electrical signal through a low pass filter to eliminate high frequency noise prior to the determination of the maxima and minima of said filtered electrical signal, said high frequency noise otherwise potentially being detected as artificial maxima or minima of said electrical signal.

14. The method of claim 13 wherein the step of determining the maxima of the filtered electrical signal comprises the step of passing the filtered signal to a peak detector to determine the maxima of the filtered signal.

15. The method of claim 14 wherein the step of determining the minima of the filtered electrical signal comprises the step of:
- inverting the filtered signal; and
- passing the inverted filtered signal to a peak detector to determine the minima of the filtered signal.

16. The method of claim 15 wherein the step of applying extreme value statistical analysis comprises the steps of:
- passing the maxima of the filtered signal to a computer via a sample and hold circuit;
- passing the minima of the filtered signal to said computer via a sample and hold circuit; and
- applying said computer to determine the statistical characteristics of said sheet material by means of extreme value statistical analysis.

17. Apparatus for determining statistical characteristics of a measurable property of sheet material comprising:
- gauge means for monitoring the property of said sheet material and for generating an electrical signal representative of variations in said property;
- high pass filter means connected to said gauge means for receiving said electrical signal and eliminating low frequency noise therefrom;
- first peak detection means connected to said high pass filter means for determining the maximum value of the filtered electrical signal;
- first sample and hold means for reading said peak detection means;
- timing means for periodically clearing said first peak detection means and said first sample and hold means; and
- analyzer means for generating statistical characteristics of the property of said sheet material by means of extreme value statistical analysis in response to maximum values of said filtered electrical signal read from said first sample and hold means.

18. The apparatus of claim 17 further comprising:
- inverter means, connected to said filter means, for inverting said filtered electrical signal;
- second peak detector means, connected to said inverter means, for determining the minimum values of said filtered electrical signal; and
- second sample and hold means for reading said second peak detector, said timing means being connected to clear periodically said second peak detector means and said second sample and hold means, and said analyzer means further generating selected statistical characteristics of the property of said sheet material in response to minimum values of said filtered electrical signals read from said second sample and hold means by means of extreme value statistical analysis.

19. The apparatus of claim 17 further comprising scanning means for moving said gauge means across said sheet material.

20. The apparatus of claim 18 further comprising scanning means for moving said gauge means across said sheet material.

* * * * *